United States Patent [19]

Greenshields et al.

[11] Patent Number: 5,151,269
[45] Date of Patent: Sep. 29, 1992

[54] TOPICAL ANESTHETIC COMPOSITION COMPRISING A CAPPED POLYOXYALKYLENE ALCOHOL

[75] Inventors: James N. Greenshields, Hockessin; Peter P. Walters, Claymont, both of Del.

[73] Assignee: Imperial Chemical Industries PLC, Wilmington, Del.

[21] Appl. No.: 229,589

[22] Filed: Aug. 8, 1988

[30] Foreign Application Priority Data

Aug. 10, 1987 [GB] United Kingdom ............... 8718886

[51] Int. Cl.$^5$ .................... A61K 7/16; A61K 7/44; A61K 7/32; A61K 7/15
[52] U.S. Cl. ..................... 424/401; 424/49; 424/59; 424/60; 424/64; 424/65; 424/70; 424/73; 424/DIG. 10; 514/830; 514/919; 106/35
[58] Field of Search ............... 424/49, 59, 60, 64, 424/65, 70, 73, 401, DIG. 10; 106/35; 523/105; 514/404, 547, 830, 919

[56] References Cited

U.S. PATENT DOCUMENTS

| | | | |
|---|---|---|---|
| 3,215,603 | 11/1965 | Gross et al. | 424/70 |
| 4,486,405 | 12/1984 | Klein | 514/845 |
| 4,584,319 | 4/1986 | Lover et al. | 514/547 |
| 4,790,989 | 12/1988 | Hunter et al. | 514/404 |

FOREIGN PATENT DOCUMENTS

| | | |
|---|---|---|
| 0644231 | 5/1964 | Belgium . |
| 1000131 | 4/1988 | Belgium . |
| 2209544 | 7/1974 | France . |
| 2141025 | 12/1984 | United Kingdom . |

OTHER PUBLICATIONS

"The Merck Index", p. 1094, Section 7449, tenth edition (1983).

*Primary Examiner*—Thurman K. Page
*Assistant Examiner*—Carlos Azpuru
*Attorney, Agent, or Firm*—William E. Dickheiser; Paul L. Sharer

[57] ABSTRACT

A composition for external use contains at least one active ingredient and a capped ethoxylated alcohol of the formula $RO(EO)_xR^1$ where R and $R^1$ are both hydrocarbon or substituted hydrocarbon and x is at least two. R is preferably a higher alkyl group and $R^1$ is a lower alkyl group. X is preferably at least 4. The ethoxylated alcohol is typically used in an amount to provide a soothing effect. The ethoxylated alcohol may be incorporated into cosmetic or pharmaceutical compositions such as shaving cream, pre- and after-shave lotions, sunburn lotions, lotions and creams for chapped lips etc., insect bite lotions etc., mouth wash, and antiperspirant.

10 Claims, No Drawings

TOPICAL ANESTHETIC COMPOSITION COMPRISING A CAPPED POLYOXYALKYLENE ALCOHOL

The present invention relates to compositions for external use and particularly to such compositions which have at least a transitory soothing effect.

Compositions for external use include both cosmetic and pharmaceutical compositions. The term "external use" is used herein to exclude compositions which are taken internally. However, compositions such as a mouth rinse are regarded herein as being for external use. Compositions of this type can be used in the form of a liquid, an emulsion or a stick composition and typically such compositions are applied topically to the skin. The composition can be, inter alia, a shaving aid such as a shaving cream or pre-shave lotion, an after-shave lotion, a burn lotion or cream such as a sunburn or windburn cream, a composition for chapped skin, for example chapped lips, an insect bite or insect repellant composition, a shampoo, a mouth rinse, an anti-perspirant or a pet care composition such as a pet shampoo. Compositions of the foregoing types may be used when there is a possibility of an irritation or after some irritation has occurred. In such cases it is desirable that the composition provides at least a transitory soothing effect to ease any irritation which may occur. We have now found a class of materials which are particularly effective in providing a soothing effect and which cause little, usually no, skin irritation.

According to the present invention there is provided a composition for external use which contains at least one active ingredient and which also contains a compound of the general formula:

$$RO(AO)_xR^1$$

wherein:

A is an alkylene group;
R is a hydrocarbon or substituted hydrocarbon;
$R^1$ is a hydrocarbon or substituted hydrocarbon; and
x has a value of at least two.

If R or $R^1$ is a substituted hydrocarbon, the substituent group can be halogen, a group $OR^2$, $SR^2$ or $NR^2R^3$, a nitro or a cyano group; and $R^2$ and $R^3$ are hydrocarbon groups, preferably alkyl groups, particularly alkyl groups containing up to 30 carbon atoms. It is preferred that R and $R^1$ are hydrocarbon groups. The group R may be a group containing at least one aromatic ring, for example a phenyl, tolyl or benzyl group. However, we generally prefer that R is an alkyl group, especially an alkyl group containing at least 6 carbon atoms and particularly an alkyl group containing at least 9 carbon atoms. The group $R^1$ may contain an aromatic ring but it is preferred that $R^1$ is an alkyl group, especially one containing not more than 5 carbon atoms, very conveniently a methyl group.

The value of x is preferably at least 4. In general the value of x is not greater than 30 and typically does not exceed 10. It will be appreciated that compounds of this type are usually a mixture of compounds in which the value of x is different. The value of x is a mean value for a mixture of compounds and x is not necessarily an integer.

The group A is typically an alkylene group containing not more than 4 carbon atoms, that is an ethylene, propylene or butylene group, and A is especially an ethylene group.

A compound of the foregoing type which has a useful combination of properties is one in which R is a mixture of alkyl groups containing 12 or 13 carbon atoms, x has a value of about 6, $R^1$ is a methyl group and A is an ethylene group.

The amount of the compound $RO(AO)_xR^1$ (hereafter the "capped ethoxylate") which is present in the composition of the present invention will be dependent on the particular capped ethoxylate which is present and also the effect required in the particular composition. In general the capped ethoxylate is present in the composition at a level intended to produce a soothing effect, particularly a transitory soothing effect. However, it should be appreciated that the effect of the composition will be dependent on the amount of the composition which is used and a greater or lesser soothing effect will be obtained in dependence on the amount of the composition which is used. The capped ethoxylates used in the compositions of the present invention are effective as topical anesthetics and typically are present in the composition in an amount sufficient to give a soothing effect under the proposed conditions of use of the particular composition. The amount of the capped ethoxylate which is present in the composition is typically from 10 ppm by weight up to 10% by weight, for example from 0.005 up to 5% by weight.

The composition can be in any suitable form for external use and may be formulated with suitable active ingredients as either a cosmetic or pharmaceutical composition, particularly one for application to treat skin complaints. Thus, the composition can be a liquid formulation, an emulsion or a stick composition. If the composition is a stick composition it is preferably one which is capable of softening and spreading on the application of heat or pressure.

The composition which contains the capped ethoxylate may be a shaving stick or shaving cream, a pre-shave lotion, an after-shave lotion, a bath additive, a shampoo including a pet shampoo, a sunburn cream or lotion, a cream or stick for chapped lips, hand cream, an insect repellant cream or an insect bite cream, a mouth rinse, an anti-perspirant or a pharmaceutical composition suitable for the treatment of skin complaints such as neurodermatitis and psoriasis. The other components of the composition, including the active ingredients, and the proportions of such other components, can be selected in accordance with the knowledge of the man skilled in the art of cosmetic and/or pharmaceutical formulations.

The invention is further illustrative by the following non-limiting Examples in which all parts are by weight except where stated to the contrary.

EXAMPLE 1

Deodorant sticks had the following composition:

|  | A | B |
| --- | --- | --- |
| Ethyl alcohol | 72.5 | 72.9 |
| Sodium stearate | 7.0 | 7.0 |
| Propylene glycol | 5.0 | 5.0 |
| Water | 10.0 | 10.0 |
| Dimethylisosorbide | 5.0 | 5.0 |

-continued

|                              | A   | B   |
| ---------------------------- | --- | --- |
| Capped ethoxylate¹           | 0.5 | 0.1 |

¹Capped ethoxylate is a compound of the type RO(AO)$_x$R¹ in which R is a mixture of alkyl groups containing 12 or 13 carbon atoms, A is an ethylene group, x has a value of about 6 and R¹ is methyl.

EXAMPLE 2

After-shave lotions had the following composition:

|                     | A    | B    |
| ------------------- | ---- | ---- |
| Ethyl alcohol       | 93.9 | 93.7 |
| Perfume             | 6.0  | 6.0  |
| HMB²                | Nil  | 0.2  |
| Capped ethoxylate¹  | 0.1  | 0.1  |

¹is as defined in Example 1.
²HMB is 2-hydroxy-4-methoxybenzophenone.

EXAMPLE 3

Sunburn creams had the following composition:

|                     | A    | B    |
| ------------------- | ---- | ---- |
| Mineral Oil         | 5.0  | 5.0  |
| Stearyl alcohol     | 0.5  | 0.5  |
| SEO-21³             | 2.0  | 2.0  |
| SEO-2⁴              | 2.0  | 2.0  |
| Water               | 90.3 | 88.5 |
| Capped ethoxylate¹  | 0.2  | 2.0  |

¹is as defined in Example 1.
²SEO-21 is a stearyl alcohol-ethylene oxide (21) condensate.
³SEO-2 is a stearyl alcohol-ethylene oxide (2) condensate.

EXAMPLE 4

Anti-chap sticks had the following composition:

|                     | A    | B    |
| ------------------- | ---- | ---- |
| Petrolatum          | 49.9 | 48.0 |
| Paraffin wax        | 35.0 | 35.0 |
| Lanolin             | 15.0 | 15.0 |
| Capped ethoxylate¹  | 0.1  | 2.0  |

¹is as defined in Example 1.

EXAMPLE 5

A mouth rinse had the following composition:

|                     | A    | B    |
| ------------------- | ---- | ---- |
| Ethyl alcohol       | 79.1 | 78.7 |
| Sodim saccharin     | 0.2  | 0.2  |
| Flavour             | 0.6  | 0.6  |
| Water               | 20.0 | 20.0 |
| Capped ethoxylate¹  | 0.1  | 0.5  |

¹is as defined in Example 1.

EXAMPLE 6

Anti-perspirant sticks had the following composition:

|                          | A    | B    |
| ------------------------ | ---- | ---- |
| Cyclomethicone (pentamer)⁵ | 53.5 | 51.7 |
| Stearyl alcohol          | 20.0 | 20.0 |
| SEO-100⁶                 | 0.2  | 0.2  |
| Bentone 34⁷              | 0.5  | 0.5  |
| Aluminium chlorohydrate  | 25.0 | 25.0 |
| Fragrance                | 0.6  | 0.6  |
| Capped ethoxylate¹       | 0.2  | 2.0  |

¹is as defined in Example 1.
⁵Cyclomethicone (pentamer) is the cyclic pentamer of [(CH$_3$)$_2$SiO].
⁶SEO-100 is a stearyl alcohol-ethylene oxide (100) condensate.
⁷Bentone 34 is a commercially available quaternised clay.

EXAMPLE 7

Soluble bath oils had the following composition:

|                     | A    | B    |
| ------------------- | ---- | ---- |
| Perfume             | 5.0  | 5.0  |
| SML⁸                | 20.0 | 25.0 |
| MHB⁹                | 0.1  | 0.1  |
| Water               | 73.9 | 59.9 |
| Capped ethoxylate¹  | 1.0  | 10.0 |

¹is as defined in Example 1.
⁸SML is sorbitan monolaurate.
⁹MHB is methyl-4-hydroxybenzoate.

We claim:

1. A composition for external use which contains at least one cosmetically or pharmaceutically active ingredient and which also contains from 10 ppm by weight up to 10% by weight of a compound of the general formula:

$$RO(AO)_xR^1$$

wherein:
A is a $C_1$–$C_4$ alkylene group;
R is phenyl, tolyl, benzyl or $C_9$–$C_{13}$ alkyl; optionally substituted with halogen, nitro, cyano, a group of the formula $OR^2$, $SR^2$ or $NR^2R^3$ wherein $R^2$ and $R^3$ are $C_1$–$C_{30}$ alkyl;
$R^1$ is phenyl, tolyl, benzyl or $C_1$–$C_{13}$ alkyl; optionally substituted with halogen, nitro, cyano, or a group of the formula $OR^2$, $SR^2$ or $NR^2R^3$ wherein $R^2$ and $R^3$ are $C_1$–$C_{30}$ alkyl; and
x has a value of 2–30.

2. The composition of claim 1 wherein $R^1$ is an alkyl group containing not more than 5 carbon atoms.

3. A composition as claimed in claim 1 wherein x is at least 4 and not greater than 30.

4. A composition as claimed in claim 1 wherein A is an ethylene group.

5. The composition of claim 1 wherein R is a mixture of alkyl groups containing 12 or 13 carbon atoms, x has a value of about 6, $R^1$ is a methyl group and A is an ethylene group.

6. The composition of claim 1 which contains from 0.005 up to 5% by weight of the compound RO-$(AO)_xR^1$.

7. A composition as claimed in claim 1 which is in the form of a liquid, an emulsion or a stick composition.

8. A composition as claimed in claim 1 which is a pharmaceutical composition for the treatment of skin complaints.

9. A composition in accordance with claim 1 wherein R is $C_9$–$C_{13}$ alkyl.

10. A composition in accordance with claim 1 wherein:
A is ethylene;
R is $C_{12}$ or $C_{13}$ alkyl;
$R^1$ is methyl; and
x equals 6.

* * * * *